United States Patent [19]

Hsu et al.

[11] Patent Number: 5,417,969
[45] Date of Patent: May 23, 1995

[54] PROCESS FOR REDUCING THE THROMBOGENICITY OF BIOMATERIALS

[75] Inventors: Li-Chien Hsu; David P. Balding, both of Mission Viejo; Lawrence Farhat, Carlsbad, all of Calif.

[73] Assignee: Baxter International Inc., Deerfield, Ill.

[21] Appl. No.: 154,654

[22] Filed: Nov. 18, 1993

Related U.S. Application Data

[63] Continuation-in-part of Ser. No. 764,554, Sep. 20, 1991, abandoned.

[51] Int. Cl.$^6$ .................. A61L 2/08; A61L 17/00; A61L 27/00
[52] U.S. Cl. .................. 424/78.27; 424/78.17; 424/423; 424/78.1; 522/126; 528/488; 422/22
[58] Field of Search ........... 424/78.08, 78.27, 78.17, 424/423, 78.1; 522/126; 528/488

[56] References Cited

U.S. PATENT DOCUMENTS

| | | | |
|---|---|---|---|
| 3,453,194 | 7/1969 | Bennett et al. | 514/56 |
| 3,625,745 | 12/1971 | Wright et al. | 128/334 |
| 4,094,756 | 6/1978 | Taylor | 522/126 |
| 4,656,083 | 4/1987 | Hoffman et al. | 428/265 |
| 4,871,357 | 10/1989 | Hsu et al. | 514/56 |
| 4,927,676 | 5/1990 | Williams et al. | 428/36 |

FOREIGN PATENT DOCUMENTS

| | | |
|---|---|---|
| 1125449 | 6/1982 | Canada. |
| 0124200 | 7/1984 | European Pat. Off. |
| 0199693 | 7/1985 | European Pat. Off. |
| WO9101767 | 2/1991 | WIPO. |

OTHER PUBLICATIONS

Chawla et al. Pharmacology 20:224–228 1980.

*Primary Examiner*—Thurman K. Page
*Assistant Examiner*—Peter F. Kulkosky
*Attorney, Agent, or Firm*—Poms, Smith, Lande & Rose; Raymond Sun

[57] ABSTRACT

Processes for forming a uniform, continuous coating of heparin covalently bonded to blood-contacting polyvinylchloride surfaces of a medical device are disclosed. These processes include coating the polyvinylchloride surfaces with an organic solvent solution of heparin complexed with an organic cation, and then exposing the coated surfaces to ionizing radiation to covalently bind the heparin moiety to the polyvinylchloride. The complex of the coating is formed from a heparin moiety and at least one cationic moiety selected from the group consisting of dimethylstearylamine, polyethyleneimine, benzalkonium, stearylkonium, and tridodecylmethylammonium; the complex is soluble in organic solvents and forms continuous and uniform coatings on polyvinylchloride. Advantageously, the heparin moiety can be bonded to the polyvinylchloride surfaces simultaneously with sterilizing the medical devices using ionizing radiation.

11 Claims, No Drawings

PROCESS FOR REDUCING THE THROMBOGENICITY OF BIOMATERIALS

This is a continuation-in-part of U.S. application Ser. No. 07/764,554, filed Sep. 20, 1991, now abandoned.

FIELD OF THE INVENTION

The present invention relates generally to a process for improving the biocompatibility of polymeric materials. More particularly, the present invention provides a process for reducing the thrombogenicity of biomaterials by directly bonding heparin to blood contacting surfaces of biomedical devices. Advantageously, the process of the present invention utilizes ionizing radiation to sterilize biomedical devices and bind heparin to their blood contacting surfaces.

DESCRIPTION OF RELATED ART

During the past several decades, synthetic polymers have found increased utility as the primary material in the fabrication of medical devices. In conjunction with this increased utility, significant advances in therapeutic and diagnostic procedures utilizing medical devices have provided the catalyst for an emerging biomaterials technology. A major effort in this field of biomaterials technology has been directed toward developing biomaterials having improved blood compatibility.

Synthetic materials such as relatively high molecular weight polymeric materials are foreign to living organisms and when used in direct contact with blood, these material induce blood coagulation and cause thrombus or clot formation. Certain types of materials have a greater tendency to form thrombi and are less biocompatible than other materials. Nevertheless, all foreign materials will induce clot formation to some extent. Thus, medical devices such as synthetic vascular grafts, cannulas, blood indwelling monitoring devices, artificial kidneys, artificial heart-lungs, extracorporeal circuits for auxiliary circulating devices, A-V shunts, vascular prostheses, artificial heart valves, temporary blood bypass tubes, and dialysis membranes are inherently thrombogenic. Any thrombi which form on the surface of these devices can stop blood flow or break away and move with the blood current. In in vivo applications, the thrombi can cause complications such as pulmonary thrombosis, cerebral thrombosis or myocardial infarction.

One approach to reducing the incidence of thrombus formation on the surface of medical devices is to systemically administer an anticoagulant such as heparin, coumarin or sodium citrate to the patient prior to implanting a medical device or bringing the patient's blood into contact with a device. A major disadvantage associated with this approach is that it significantly prolongs the patient's blood clotting time. Should the patient be injured with either external or internal bleeding, the consequences of a prolonged clotting time can be a serious excessive loss of blood before sufficient clotting takes place to stop the bleeding.

Another approach to solving the problem associated with the thrombogenicity of medical devices is to alter the surface of the blood contacting surfaces to reduce thrombogenic activity. In particular, a number of researches have attempted to physically or chemically bind heparin to the surface of biomaterials in order to reduce thrombogenicity. Since heparin is a highly hydrophilic mucopolysaccharide and insoluble in organic solvents, in order to coat a solid surface with heparin it must be applied from an aqueous solution. Polymeric materials, on the other hand, are largely hydrophobic and aqueous solutions applied to these surfaces bead-up and fail to form even, continuous films. Thus, attempts to physically bind heparin to these hydrophobic surfaces result in uneven and ineffective applications. Moreover, for the same reason, attempts to chemically bind heparin to polymeric surfaces result in the same uneven and nonuniform heparin deposits.

Other attempts to bind heparin to hydrophobic polymeric surfaces include first coating the biomaterial surface with a hydrophilic material which is soluble in organic solvents. Then, an even heparin coating can be applied directly to the hydrophilic surface. Additionally, some researchers have covalently bonded heparin to the hydrophilic coating by selecting a hydrophilic coating having functionalities which are reactive to heparin. This approach to improving the blood compatibility of biomaterials has generally not met with success. The hydrophilic pre-coating is not covalently bonded to the surface of the biomaterial. Thus, regardless of whether or not the heparin is covalently bound to the pre-coating, the physical link between the pre-coating and the surface of the biomaterial weakens and the heparin escapes from the surface. Moreover, reacting the mucopolysaccharide moiety with the hydrophilic coating alters the mucopolysaccharide, resulting in a reduced activity.

Additional attempts to bind heparin to biomaterial surfaces have focused on providing an association of a hydrocarbon and heparin in order to enhance its ability to physically coat polymeric surfaces. In one of these associations the heparin anion is complexed with an organic cation. This is possible because heparin's mucopolysaccharide structure is anionic with both sulfonic acid and carboxylic acid functionalities. In its sodium salt form, heparin anion can associate with other cations, such as quaternary ammonium cations and tertiary amines, capable of exchanging with sodium. Many of these cations have significant hydrophobic features and when associated with the heparin anion will readily dissolve in organic solvents such as alcohols. Films of these heparin associations can be uniformly applied to the surfaces of many polymers used in medical devices. The integrity and stability of these films however are dependent upon the strength of the association between heparin and the cation. The ionic association of the cation and heparin anion must be sufficiently high to preclude blood from exchanging with the cation-heparin association and removing heparin from the surface of the polymer. The most significant advantage of these heparin associations are that the heparin mucopolysaccharide is not altered in any way and the heparin retains its anticoagulant activity.

Some quaternary ammonium heparin associations have met with approval in the medical community. Notably benzalkonium heparin, stearylkonium heparin and tridodecylmethylammonium heparin associations have relatively high ionic strengths and a significant amount of the associations remain intact in the presence of blood. Additionally, films of these quaternary ammonium salt heparin associations physically adhere to many biomaterials and retain much of their anticoagulant activity. These films can however be removed using mechanical forces and excess handling will cause a significant loss of surface anticoagulant activity.

Another association of a hydrocarbon and heparin is an acid-base complex of the heparin acid functionalities and an organic base such as a tertiary amine. These acid-base complexes have the same advantageous film-forming properties and dissolution properties. Particularly well-known acid-base complexes are dimethylstearylamine heparin and polyethyleneimine heparin complexes.

Many researchers and practitioners within the medical device industry have generally recognized that covalently bonding heparin to the surface of biomaterials is a superior approach to producing antithrombogenic medical devices. A number of techniques have been utilized to covalently link heparin to polymers. One of these involved milling heparin powder in silicone or applying aqueous solutions of heparin to the surface of silicone devices and then irradiating the device with ionizing radiation. As mentioned above, however, aqueous solutions of heparin do not wet the hydrophobic silicone surfaces. Thus, this method does not provide uniform continuous coatings of heparin and any heparin which may deposit on the surface appears in isolated deposits.

Another covalent bonding technique utilizes polymeric surface grafting processes to provide active chemical functionalities on the polymeric surface which will react with heparin. Then exposing heparin solutions to these functionalities causes heparin to bind to the active functionalities. These techniques, however, result in insufficient surface anticoagulation activity which is attributed to both small amounts of heparin bonded to the surface and heparin modification. The heparin modification occurs because polysaccharide functionalities which contribute to the anticoagulation properties of the heparin are modified when they react with functionalities on the polymeric surface.

Other similar approaches include derivatizing the heparin molecule itself to provide specific reactive functionalities for covalently bonding to the surface of a medical device. For the same reasons described above, this approach also suffers from insufficient anticoagulant activity on the polymeric surface. Believing that part of the reduction in activity may be caused by conformational restraints on the immobilized heparin molecule, some researches have modified heparin to include large spacer molecules or leashes which can be attached to polymer surfaces. This approach also results in a chemically modified heparin polysaccharide having reduced anticoagulant activity.

A common problem associated with all of these attempts to provide antithrombogenic surfaces for medical devices stems from the fact that any one device is rarely made from a single type of polymer. Thus, effectively developing and manufacturing heparin treated surfaces for all of the polymers utilized in a single device is very costly. Additionally, since all medical devices must be sterilized, antithrombogenic surfaces on polymers must retain sufficient amounts of activity subsequent to sterilization. Most medical devices are sterilized using a gas such as ethylene oxide or ionizing radiation. Thus, the form in which the anticoagulant agent is retained on the surface of the polymer must be sufficiently stable to remain active subsequent to sterilizing and for a reasonable shelf life.

Accordingly, it is an object of the present invention to provide a process for enhancing the antithrombogenic activity of biomaterials and medical devices.

It is also an object of the present invention is to provide a process for covalently bonding anticoagulants uniformly to the surface of biomaterials and medical devices.

It is additionally an object of the present invention to provide a process for simultaneously sterilizing and enhancing the antithrombogenic activity of medical devices.

A further object of the present invention is to provide an anticoagulant bonding process which does not cause significant loss in anticoagulant activity.

Another object of the present invention is to provide biomaterials having sustained antithrombogenic activity in the presence of blood and other high ionic strength fluids.

SUMMARY OF THE INVENTION

In its broadest aspect, the present invention accomplishes the above objectives by providing a process for chemically binding anticoagulants to biomaterials. The process of the present invention is directed toward chemically binding heparin to surfaces of biomaterials in order to provide medical devices which can be used in direct contact with blood without causing platelet aggregation and the formation of thrombi. Moreover, heparin which is bonded to medical devices in accordance with the present invention retains significant anticoagulant activity and does not leach, hydrolyze or otherwise dissociate from the surface of medical devices.

More particularly, the present invention provides a method for reducing the thrombogenicity of biomaterials by providing biomaterials having a surface coating of anticoagulant and exposing the coated biomaterials to sufficient ionizing radiation to chemically bind the anticoagulant to the biomaterial. Preferably, the anticoagulant coating is a uniform continuous film of heparin. The heparin is initially coated on the device in the form of a complex composed of the heparin anion and an organic cation. Suitable organic cations are selected from the group consisting of quaternary ammonium salts and organic bases such as amines. Many ionic complexes of heparin and quaternary ammonium cations are commercially available from a number of sources. Others can be prepared by combining sodium heparin and the selected quaternary ammonium salt in an appropriate solvent and collecting the precipitated ionic complex. Similarly, organic amines readily form an acid-base complex with heparin by combining a solution of heparin with a solution of the appropriate amine.

Further, in accordance with the present invention, providing biomaterial having an anticoagulant coating can be accomplished by allowing the biomaterial to contact organic solvent solutions of the ionic complex in order to deposit a film of the solution on the surface of the biomaterial. Typically, the liquid solutions include the ionic complex in a volatile organic solvent which readily vaporizes at ambient temperatures and pressures leaving a coating of the ionic complex on the surface of the biomaterial.

After allowing the solvent to vaporize, exposing the coated biomaterial to ionizing radiation can be accomplished using any ionizing radiation source including gamma radiation sources, electron beam sources, and x-ray sources. Although radiation doses of as low as 0.1 megarad are sufficient to chemically bond heparin to polymeric biomaterials, it is common to use higher sterilizing doses of radiation. This advantageously provides a sterile biomaterial and the anticoagulant activity of the bonded heparin remains sufficiently high even after exposure to the higher radiation doses.

As a feature of the present invention, following exposing the coated biomaterials to ionizing radiation, the process of the present invention can further include contacting the coated biomaterial with a high ionic strength salt solution. As described in more detail below, this step results in the exchange of the cation of the ionic complex with a much less toxic cation of the salt solution. Moreover, the process can further include exposing the coated and exchanged biomaterial to sterilizing doses of ionizing radiation without significantly reducing the anticoagulating activity of the surface of the biomaterial. Advantageously, the thrombogenicity of medical devices fabricated from a variety of biomaterials can be reduced in accordance with the teachings of the present invention.

Further objects, features and advantages of the process of the present invention, as well as a better understanding thereof, will be afforded to those skilled in the art from a consideration of the following detailed explanation of preferred exemplary embodiments thereof.

DETAILED DESCRIPTION OF PREFERRED EMBODIMENTS

The present invention provides a process for reducing the thrombogenicity of medical devices by chemically binding anticoagulant to the surfaces of biomaterials utilized in medical devices. The invention disclosed herein is described in terms of chemically binding heparin to the surfaces of polymeric materials having utility as biomaterials in fabricating blood contacting surfaces of medical devices. Those skilled in the art, however, will appreciate that the processes taught herein are applicable, in general, to chemically binding polysaccharides, mucopolysaccharides, glycoproteins, and related compounds to polymeric materials.

The present invention is based upon the surprising discovery that materials which are first coated with organic solutions of heparin ionically complexed with an organic cation and then exposed to ionizing radiation, retain high antithrombogenic activity even after being subjected to severe techniques for removing the heparin from the surface. In accordance with the present invention, biomaterials can be uniformly and continuously coated with heparin without modifying or derivatizing the mucopolysaccharide moiety. Accordingly, the heparin mucopolysaccharide moiety remains intact and its anticoagulant activity is not compromised.

More specifically, the present invention provides a method for reducing the thrombogenicity of polyvinylchloride surfaces of a medical device by coating those surfaces with an organic solution of heparin ionically complexed with an organic cation, and exposing the coated polyvinylchloride surface to sufficient ionizing radiation to covalently bind the heparin to the polymeric material. Preferably, subsequent to the coating step, the solvent is allowed to vaporize from the coated surface. Then exposing the coated surface to ionizing radiation is typically accomplished with standard gamma irradiation sterilizing procedures using cobalt[60] or cesium[137] sources. However, other types of ionizing radiation such as electron beam and x-rays are also applicable. The ionizing radiation causes covalent bond formation between the polyvinylchloride and the heparin moiety. The cationic moiety of the complex may then be stripped from the surface with a high ionic strength solution as described below.

Polymeric materials having utility in the present invention are solid organic polymers in the form of shaped articles, powders, granules, pellets, films, fibers or foams. Preferably, the polymeric materials are biomaterials in the form of medical devices used for in vivo, ex-vivo and in vitro diagnostic and therapeutic procedures. Examples of these include blood contacting medical devices such as synthetic vascular grafts, catheters, cannulas, blood indwelling monitoring devices, artificial kidneys, artificial heart-lungs, extracorporeal circuits for auxiliary circulating devices, A-V shunts, vascular prostheses, artificial heart valves, temporary blood by-pass tubes, and dialysis membranes.

Additionally, polymeric materials having utility in the practice of the present invention retain sufficient physical integrity to perform their intended function following exposure to ionizing radiation in amounts sufficient to chemically bind heparin. The most preferred polymeric material to be used in this invention is polyvinylchloride containing a plasticizer. Suitable plasticizers are diethylhexylphthalate (DEHP), dioctyladipate (DOA), and trioctyltrimilletate (TOTM). Herein, the term "polyvinylchloride" encompasses all forms of polyvinylchloride, including those containing plasticizers. Typically, plasticized polyvinylchloride is used to make medical grade flexible tubing. As described in more detail below, the amount of ionizing radiation received by the polymeric material can vary, but is typically at least 1 megarad.

In accordance with the present invention, suitable forms of heparin are complexes of heparin and an organic cation moiety which have sufficient hydrophobic or lipophilic properties to render the complex soluble in organic solvents. One type of heparin/organic cation complex having utility in the present invention is a complex in which the acidic moieties of the heparin mucopolysaccharide and a suitable organic base (the cation) form an acid-base complex. Primary, secondary, or tertiary amines are organic bases known to form acid-base complexes with heparin. Particularly suitable organic bases are dimethylstearylamine and polyethyleneimine, which form dimethylstearylamine-heparin and polyethyleneimine-heparin complexes, respectively, with heparin.

Other suitable heparin/organic cation complexes having utility in the present invention are ionic complexes in which the heparin mucopolysaccharide anion and a suitable organic cation form an ion pair. Particularly suitable organic cations are quaternary ammonium salt cations including benzalkonium, stearylkonium, and tridodecylmethylammonium cations. In accordance with the present invention, preferred heparin/organic cation complexes are benzalkonium-heparin, stearylkonium-heparin, and tridodecylmethylammonium-heparin complexes.

Herein, the term "organic cation moiety" encompasses bases, such as amines, as well as quaternary ammonium salts. Many of the quaternary ammonium-heparin ionic complexes are commercially available. Others can be prepared by combining sodium heparin and the selected quaternary ammonium salt in an appropriate solvent or combination of solvents. Typically, a quaternary ammonium-heparin ionic complex will quickly precipitate from the solvent. For example, benzalkonium-heparin can be prepared by combining aqueous solutions of benzalkonium chloride and sodium heparin.

The benzalkonium-heparin ionic complex precipitates cleanly upon formation and the resulting complex can be dissolved in lower organic alcohols, such as isopropyl alcohol.

In accordance with the present invention, contacting a polymeric material with an organic solvent solution of heparin can be accomplished using any of a variety of methods including dipping the polymeric material in the solution, spraying the solution onto the polymeric material, flushing tubing with the solution, dropping solution onto the polymeric material, and brushing the solution. Typically, the contacting step is carried out for a length of time sufficient to deposit an anticoagulating amount of heparin on the polymeric material. As will be described in more detail below, the amount of heparin deposited on the polymeric material is also dependent upon the concentration of the heparin in the organic solvent solution.

The choice of organic solvent is dependent upon the solubility of the organic compound-heparin complex. Preferably, the organic solvent does not dissolve or chemically react with the polyvinylchloride material. Organic solvents capable of swelling selected polymers are preferred in some applications in which heparin is desirably physically immobilized by swelling the polymer and locking in the heparin. Additionally, the solvent should be nonreactive with the organic compound-heparin complex and preferably has a high vapor pressure for ease in vaporizing the solvent subsequent to dipping, spraying, flushing, or brushing. Suitable solvents are lower alkyl alcohols, halohydrocarbons, combinations of halohydrocarbons and alcohols, hydrocarbons, ethers, ketones, dimethylformamide, dimethylsulfoxide, and dimethylacetamide. For instance, n-propanol can be used as the solvent, as can a mixture of hexane and isopropyl alcohol.

The organic cation-heparin anion complex is typically present in the organic solvent solution at from about 0.01 wt % to about 10 wt %. The preferred concentration depends upon the particular type of polymeric material utilized and the desired amount of heparin coating. The concentration of organic cation-heparin anion complex in the organic solvent solution correlates with the amount of complex which is coated on the polymeric material. Thus, the higher the concentration of the complex, the higher the amount of coating. Also, some polymeric materials have surface characteristics which cause higher amounts of complex to coat.

As just mentioned, suitable concentrations of the organic compound-heparin complex can also depend upon the desired amount of organic compound-heparin complex coating on the polymeric material. The preferred amount of coating is an anticoagulating amount and this anticoagulating amount primarily depends upon the specific function of the polymeric material. Polymeric materials utilized as biomaterials in medical devices which function for prolonged periods in contact with blood will preferably have higher amounts of coating. Accordingly, organic solvent solutions utilized to coat these biomaterials will have higher concentrations of complex. Alternatively, to provide more coating, the step of contacting the biomaterials with the organic solvent solution can be carried out a plurality of times. Generally speaking, an anticoagulating amount of organic cation-heparin anion complex coating on biomaterials is from about 0.1 micrograms/cm$^2$ to about 40 micrograms/cm$^2$. Additionally, for most applications, the preferred concentrations of organic cation-heparin anion complex in organic solvent solution is about 0.5 wt %.

As mentioned above, in accordance with the present invention, the coated polymeric material is exposed to sufficient ionizing radiation to chemically bind heparin to the polymeric material. This amount of radiation can be as low as 0.1 megarad. Moreover, exposing the polymeric material to sterilizing doses of higher than 3 megarads does not significantly reduce the anticoagulant activity of the chemically bonded heparin. As long as the final anticoagulating activity of the polymeric material is sufficiently high for the intended function of the polymeric material and the polymeric material itself is not adversely effected, any dose of ionizing radiation can be used.

Because sterilizing doses of ionizing radiation can be utilized during the exposure step, the present invention also provides a process which simultaneously reduces the thrombogenicity of medical devices and sterilizes the medical devices. Accordingly, forming a coating of an organic solvent and of an organic compound-heparin complex on the medical device, allowing the organic solvent to vaporize, and exposing the coated medical device to ionizing radiation can produce a sterile antithrombogenic medical device with heparin chemically bonded to the surface of the medical device.

As mentioned above, the process of the present invention is applicable to a variety of polymeric materials having utility as biomaterials in the fabrication of medical devices. Accordingly, forming a coating of an organic solvent and an organic compound-heparin complex can be accomplished on medical devices which are fabricated from different biomaterials using a single dipping, spraying, flushing, or brushing step as previously described. Typically, there is no requirement to treat each type of biomaterial separately. Additionally, although it is frequently convenient to form the coating of the complex of organic compound and heparin anion in a manner which coats many surfaces of the medical device, the relevant surfaces are the blood contacting surfaces of the medical device. Accordingly, a single extracorporeal circulation device can include a polycarbonate housing and silicone or polyvinylchloride tubing. All of these biomaterials when incorporated in the circulation device have blood contacting surfaces which can be simultaneously coated with heparin by flushing the blood contacting surfaces with a quaternary ammonium cation and heparin anion. A preferred solution is a Freon ® solution of about 0.5 wt % stearylkonium heparin.

As mentioned above, organic solvents having utility in the process of the present invention preferably have high vapor pressures. Thus, allowing the organic solvent to vaporize typically occurs very quickly under ambient conditions. However, small amounts of flowing dry nitrogen can hasten the process.

As already mentioned, the preferred organic cation-heparin anion complexes utilized in the practice of the present invention have hydrophobic and lipophilic characteristic which render them soluble in organic solvents. Moreover, the combination of organic solvent and organic cation-heparin anion complex "wets" and coats the polymeric materials and medical devices in a uniform and continuous manner. Thus, subsequent to allowing the organic solvent to vaporize, an organic cation-heparin anion coating forms which is uniform and continuous. This feature provides medical devices with coated surfaces, and more importantly coated blood contacting surfaces, which are uniformly antithrombogenic. These coatings are unlike prior art "coatings" of nonderivatized heparin which are noncontinuous and non-uniform deposits of heparin.

Sometimes it is preferable to simultaneously chemically bind heparin to medical devices and sterilize the medical devices. Therefore, prior to exposing the medical devices to ionizing radiation, the processes of the present invention further include packaging the medical devices in sterile packaging or packaging suitable for maintaining sterility after a sterilizing procedure. Then, exposing the packaged medical device to ionizing radiation includes exposing the package to sufficient ionizing radiation to sterilize the medical device and chemically bind heparin to the medical device. Typically, total ionizing radiation doses of at least 2.5 megarads are required to meet the standards for sterility. However, doses as low as 1.5 megarads can be used as well.

A particularly advantageous feature of an alternative embodiment of the present invention is based upon the discovery that it is largely the heparin anion which is chemically bonded to polymeric material following the exposure to ionizing radiation. When the heparin complex of the present invention is an organic cation-heparin anion complex, the organic cation remains ionically associated with the heparin anion and it is not significantly covalently or otherwise directly bonded to the polymer material. Thus, by contacting the coated surfaces of the radiation exposed medical device with liquid solution having an ionic strength sufficiently high to exchange organic cation with a cation in the liquid solution, organic cation can be removed from the medical device without removing heparin anion. This step provides for exchanging cations, such as benzalkonium or stearylkonium cations or stearyldimethylamine, which have less desirable biocompatible characteristics, for a cation such as sodium having a high degree of biocompatibility.

Thus, an alternative to simultaneously binding heparin to a medical device and sterilizing the medical device is a process which includes forming a coating of an organic cation-heparin anion complex on the medical device and exposing the coated medical device to sufficient ionizing radiation to bind the heparin anion to the medical device. The next steps include exchanging the organic cation with a highly biocompatible cation, packaging the medical device in appropriate packaging for maintaining sterility, and sterilizing the medical device. This sterilizing step is preferably accomplished by exposing the medical device to a total dose of at least 1.5 megarads of ionizing radiation. However, other suitable sterilizing procedures including exposure to sterilizing gases and heat can also be used when applicable.

Liquid solutions having sufficiently high ionic strengths include solutions of 20 wt % NaCl and aqueous buffered solutions of surfactants.

In an exemplary embodiment of the present invention, polyvinylchloride tubing can be coated on the interior walls of the tubing by flushing the tubing with a Freon ® solution of 0.5 wt % stearylkonium-heparin for 30 seconds and allowing the Freon ® to vaporize. Then, packaging the tubing and exposing the packaged tubing to from 2.5 megarads to 3.0 megarads of ionizing radiation emitted from a cobalt$^{60}$ source produces sterile polyvinylchloride tubing having nonthrombogenic interior walls.

In another exemplary embodiment of the present invention, silicone tubing can be coated on the interior walls by flushing the tubing with an isopropyl alcohol solution of about 0.5 wt % benzalkonium-heparin for about 30 seconds. Then, exposing the coated tubing to about 1 megarad of gamma irradiation from a cobalt$^{60}$ source produces silicone tubing having chemically bonded benzalkonium-heparin. Then soaking the exposed tubing in an aqueous solution of 20 wt % NaCl exchanges the benzalkonium cations for sodium cations resulting in silicone tubing having chemically bonded sodium heparin.

The mechanism of this binding procedure is not precisely known. However, it is speculated that the radiation causes free radicals to form on both the polymeric material and the heparin. Once formed, if a free radical on the polymeric material is in close enough proximity to a free radical on the heparin, they can combine to form a covalent bond. The required amount of radiation can vary depending upon the type of polymeric material and the amount of heparin coating.

The following non-limiting examples further illustrate methods for preparing the polymeric materials having reduced thrombogenicity as well as present data which substantiate the covalently bonded nature of the heparin.

EXAMPLE 1

Twelve pieces of silicone tubing having an O.D. of ⅛" and an I.D. of 1/16" were coated with stearylkonium heparin by flushing and draining the tubing with a Freon TE ® solution of 0.5 wt % stearylkonium heparin. Three of the silicone tubing pieces were used as nonirradiated control samples, three pieces were exposed to a total dose of 0.5 megarads gamma irradiation, three were exposed to 1.0 megarads, and three pieces were exposed to 3.0 megarads. The samples were evaluated by first flushing them with a salt and surfactant extract solution at 100 mL/minute for 2 hours. The salt and surfactant extract solutions were then evaluated for heparin using the $X_a$ inhibition assay. Using the nonirradiated samples as a control, the amount of heparin bonded to each group of three treated silicone samples was taken as the difference between the heparin found in the control samples and the heparin found in the irradiated sample.

The flushed silicone tubing samples were then evaluated for surface immobilized heparin by a thrombin uptake technique. This procedure consisted of pipetting 1.0 mL aliquots of 10 NIH unit/mL thrombin in an albumin-tris saline solution into 56 cM of tubing which was sealed with a sleeve and rotated on a slanted turntable for 10.0 minutes. The thrombin solution was then decanted from the tubing and assayed for thrombin.

Table I illustrates the results of the $X_a$ inhibition assay for heparin and the thrombin assay. The thrombin assay is expressed as the calculated amount of thrombin uptake in units/cm$^2$.

TABLE I

| SAMPLE | Stearylkonium heparin extracted ug/cm2 n = 3 | % retained in tubing % | Thrombin uptake U/cm2 n = 3 |
| --- | --- | --- | --- |
| No coating | — | — | 0 |
| Control/ no radiation | 25.9 ± 4.9 | — | 0.007 |
| 0.5 Mrad | 25.7 ± 4.5 | 1 | 0.005 |

TABLE I-continued

| SAMPLE | Stearylkonium heparin extracted ug/cm2 n = 3 | % retained in tubing % | Thrombin uptake U/cm2 n = 3 |
|---|---|---|---|
| 1.0 Mrad | 11.3 ± 30.6 | 56 | 0.006 |
| 3.0 Mrad | 0 | 100 | 0.018 |

The results shown in Table I indicate that more than 0.5 Mrad is required to bind a portion of the heparin to the silicone.

EXAMPLE 2

Twelve samples each of polyvinylchloride (PVC) tubing having ⅛" O.D. and 1/32" I.D., polypropylene (PP) tubing having ⅛" O.D. and 1/16" I.D., and polyethylene (PE) tubing having 2.92 mm I.D. and 3.73 mm O.D., were coated with stearylkonium heparin and evaluated using the same coating and evaluation techniques described for Example 1. Table II illustrates the results of the $X_a$ inhibition assay for heparin and the thrombin assay. The thrombin assay is expressed as the calculated amount of thrombin uptake in units/cm².

TABLE II

| SAMPLE | Theoretical amount deposited | Stearylkonium heparin extracted ug/cm2 n = 3 | % retained on tubing % | Thrombin uptake U/cm2 n = 3 |
|---|---|---|---|---|
| PVC Tubing | | | | |
| No coating | — | — | — | 0 |
| Control/ no radiation | 4 | 2.9 | — | 0 |
| 0.5 Mrad | 4 | 0.8 | 72 | 0.005 |
| 1.0 Mrad | 4 | 0.6 | 80 | 0.012 |
| 3.0 Mrad | 4 | 0 | 100 | 0.06 |
| PP Tubing | | | | |
| No coating | — | — | — | 0 |
| Control/ no radiation | — | 17.9 ± 3.0 | — | 0.007 |
| 0.5 Mrad | — | 16.3 ± 5.4 | 9 | 0.006 |
| 1.0 Mrad | — | 16.4 ± 4.6 | 8 | 0.008 |
| 3.0 Mrad | — | 16.8 ± 3.5 | 6 | 0.009 |
| PE Tubing | | | | |
| No coating | — | — | — | 0 |
| Control/ no radiation | — | 17.9 | — | 0.002 |
| 3.0 Mrad | — | 17.5 | 2 | 0.003 |
| 5.0 Mrad | — | 15.4 | 14 | 0.007 |

The results shown in Table II indicate that increasing amounts of heparin bind to polyvinylchloride over a radiation dose range of 0.5–3.0 Mrad. Moreover, the bound heparin is active (see thrombin uptake results). Polypropylene and polyethylene tubing, however, retained only small portions of heparin after exposure to gamma irradiation, and anticoagulant activity was negligible even after a radiation dosage as high as 5.0 Mrad.

EXAMPLE 3

Twelve polycarbonate connectors were dipped into a Freon TE ® solution of 0.5 wt % stearylkonium heparin and dried. Three of the connectors were exposed to a total dose of 0.5 megarad of gamma irradiation, three were exposed to a total dose of 1.0 megarad of gamma irradiation, and three were exposed to a total dose of 3.0 megarads of gamma irradiation. The twelve polycarbonate connectors were then evaluated according to the same procedures described in Example 1. Table III illustrates the results of the $X_a$ inhibition assay for heparin and the thrombin assay. The thrombin assay is expressed as the calculated amount of thrombin uptake in units/cm².

TABLE III

| SAMPLE | Theoretical amount deposited | Stearylkonium heparin extracted ug/cm2 n = 3 | % retained on connector % | Thrombin uptake U/cm2 n = 3 |
|---|---|---|---|---|
| Polycarbonate Connectors | | | | |
| No coating | — | — | — | 0 |
| Control/ no radiation | — | 0.61 ± 0.10 | — | 0.021 |
| 0.5 Mrad | — | 0.56 ± 0.10 | 8 | 0.019 |
| 1.0 Mrad | — | 0.60 ± 0.14 | 2 | 0.018 |
| 3.0 Mrad | — | 0.45 ± 0.04 | 26 | 0.014 |

The results shown in Table III indicate that 3 Mrad were required to bind a portion of the heparin to polycarbonate; however, radiation did not increase the thrombin uptake activity of polycarbonate coated with heparin.

EXAMPLE 4

Three pieces of polyvinylchloride tubing having a ¼" I.D. were flushed and drained with a Freon TE ® solution containing 0.5 wt % benzalkonium heparin (BKH). Following coating with benzalkonium heparin, the three tubing pieces were exposed to 3.0 megarads of gamma irradiation. The samples were evaluated using the techniques described in Example 1 above.

Table IV illustrates the results for the thrombin assay. The thrombin assay is expressed as the calculated amount of thrombin uptake in units/cm².

TABLE IV

| SAMPLE | Thrombin uptake U/cm² |
|---|---|
| PVC Tubing BKH treated 3.0 Mrad | 0.047 |

The thrombin uptake data results shown in Table IV indicate that polyvinylchloride which is coated with benzalkonium heparin, exposed to gamma irradiation and extracted with a high ionic strength solution retains surface anticoagulating activity.

EXAMPLE 5

Stearylkonium heparin was labelled on the stearylkonium moiety with $C^{14}$. Ten feet of polyvinylchloride tubing having a ⅜" I.D. was flushed with a Freon TE ® solution of 0.5 wt % $C^{14}$ labelled stearylkonium heparin (SKH) such that between 2.4 mg and 3.6 mg of stearylkonium moiety coated the PVC tubing. After exposure to ionizing radiation, the polyvinylchloride tubing was soaked in protein solution for 24 hours to remove stearylkonium ions. During the 24 hour soak, samples were taken and analyzed for stearylkonium content using a $C^{14}$ counting method. Two samples were collected at each time interval.

Table V indicates the results obtained for each sample analyzed for C14 content.

TABLE V

C-14 SK moiety leaching

| Time | SK (mg) leached into protein solution |
|---|---|
| 5 min | 1.05, 1.73 |
| 10 min | 1.57, 1.47 |
| 20 min | 2.57, 2.12 |
| 1 hr | 2.56, 2.69 |
| 2 hr | 2.45, 3.08 |
| 18 hr | 2.71, 4.03 |
| 24 hr | 2.39, 3.94 |

The results shown in Table V illustrate that the stearylkonium moiety was not retained by the surface of the polyvinylchloride but was substantially extracted by the salt solution after 24 hours.

EXAMPLE 6

Thirty strips of diethylhexylphthalate plasticized polyvinylchloride having a surface area of approximately 60 cm$^2$ were coated with stearylkonium heparin by manually depositing a controlled quantity of a Freon TE ® solution of 0.5 wt % stearylkonium heparin on the surface of the strips. Half of these samples were irradiated to a total dose of 3.5–4.0 megarads. Table VI details the approximate amount of stearylkonium heparin deposited on each of 10 groups of three strips and the total dose of gamma irradiation received by the strips.

TABLE VI

| Group I: | 3 ug/cm$^2$, no gamma exposure |
|---|---|
| Group II: | 3 ug/cm$^2$, 3.5–4.0 Mrad |
| Group III: | 5 ug/cm$^2$, no gamma exposure |
| Group IV: | 5 ug/cm$^2$, 3.5–4.0 Mrad |
| Group V: | 10 ug/cm$^2$, no gamma exposure |
| Group VI | 10 ug/cm$^2$, 3.5–4.0 Mrad |
| Group VII: | 15 ug/cm$^2$, no gamma exposure |
| Group VIII: | 15 ug/cm$^2$, 3.5–4.0 Mrad |
| Group IX: | 50 ug/cm$^2$, no gamma exposure |
| Group X: | 50 ug/cm$^2$, 3.5–4.0 Mrad |

Each of the thirty strips were soaked in aqueous solutions of 20 wt % NaCl to extract all cations and heparin complexes which were not chemically bonded to the polyvinylchloride. The aqueous solutions were then assayed for heparin using $X_a$ inhibition assay. Table VII illustrates the amount of heparin which was not extracted by the soaking procedure for each of the samples. This amount is the amount retained and bonded to the polyvinylchloride samples.

TABLE VII

| Samples | Detected in NaCl solution - (ug/cm2) | Percent Retained on PVC |
|---|---|---|
| Group I | 3.5 ± 0.5 | |
| Group II | 1.2 ± 0.3 | 66 ± 9 |
| Group III | 2.6 ± 0.5 | |
| Group IV | 1.1 ± 0.2 | 58 ± 8 |
| Group V | 4.7 ± 0.6 | |
| Group VI | 3.3 ± 0.8 | 30 ± 17 |
| Group VII | 11.8 ± 1.7 | |
| Group VIII | 10.2 ± 1.7 | 14 ± 14 |
| Group IX | 43.5 ± 3.2 | |
| Group X | 42.2 ± 5.0 | 3 ± 11 |

These results strongly indicate that heparin is not extracted from the surface of the polyvinylchloride but is retained or chemically bonded to the surface of the polyvinylchloride. Coating over 5 μg/cm$^2$ did not appreciably increase the absolute amount of heparin retained on the surface, suggesting that only the innermost layer of heparin was covalently bound to the surface.

EXAMPLE 7

Polyvinylchloride (PVC) articles were soaked for 15 seconds with a Freon TE ® solution of 0.5 wt % stearylkonium heparin. Half the articles were exposed to 3.5–4.0 megarads of gamma irradiation. Additionally, an equal number of polyvinylchloride articles were not soaked in the stearylkonium heparin solution. Of these, half were exposed to 3.5–4.0 megarads of gamma irradiation. Table VIII illustrates each group of samples and their treatments.

TABLE VIII

| Group I: | PVC ⅜", no gamma exposure |
|---|---|
| Group II: | PVC ⅜", with 3.5 = 4.0 mrad |
| Group III: | PVC ⅜", stearylkonium heparin treated, no gamma exposure |
| Group IV: | PVC ⅜", stearylkonium heparin treated, with 3.5–4.0 Mrad |

All of the polyvinylchloride articles were filled with 3.0 mL of non-heparinized bovine blood at 37° C. and the blood was observed for the amount of time required to coagulate. Table IX illustrates the coagulation time for each group of samples.

TABLE IX

Coagulation Time of Fresh Non-heparinized Bovine Blood for PVC samples

| Sample | Coagulation Time (min) | | |
|---|---|---|---|
| Group I | —, | 38, | 50 |
| Group II | 45, | 47, | 54 |
| Group III | >60*, | >75, | >75 |
| Group IV | >75, | >75, | >75 |

*sample stopped after 60 minutes

The results indicate that stearylkonium heparin coated polyvinylchloride is effective for extending the blood clotting time of bovine blood in contact with the coated PVC. Thus, exposure to gamma irradiation did not diminish the anticoagulant effect of the heparin coating.

EXAMPLE 8

Four 10 foot segments of polyvinylchloride tubing having a O.D. of ⅜" were coated with stearylkonium heparin by flushing and draining the tubing with a Freon TE ® solution of 0.5 wt % stearylkonium heparin. Two of the 10 foot segments were exposed to a total dose of 3.5–4.0 megarads of gamma irradiation. Each of the 10 foot segments was then leached with a 20 wt % NaCl solution by flowing the solution through the tubing at 4 liters/minute for 2 hours. The solutions were then assayed for heparin using a chemical assay method which depends upon heparin complexing with Azure A dye. The solutions used to leach the nonirradiated samples contained enough heparin to correspond to a surface coverage of 4.1 micrograms/cm$^2$. The solutions used to leach the irradiated samples showed no heparin. The results of this test indicates that heparin which was coated on the tubing samples which were irradiated was not leached off but remains bonded to the surface.

EXAMPLE 9

A 100 ml sample of 3% (wt/vol) sodium heparin solution was added into 80 ml of toluene containing 30 grams of stearyldimethyl amine with vigorous agitation. After mixing thoroughly, the solution was allowed to settle until the organic layer (toluene) separated from the aqueous layer. Stearyldimethyl amine-heparin complex formed in toluene was used to coat plasticized polyvinylchloride (PVC) tubing. The coated tubing was subsequently subjected to gamma irradiation (2.5 to 3.0 Mrad). The coated and gamma-irradiated tubing was then exposed to 20% NaCl solution to remove heparin not covalently attached to the surface. The heparin activity on the surface was evaluated by a thrombin uptake technique. The surface (55 $cm^2$) was first exposed to 2 ml of 0.5 U antithrombin III/ml. The surface was rinsed to remove unbound antithrombin III and subsequently exposed to thrombin solution (10 U/ml). The results shown in Table X are expressed as the calculated amount of thrombin uptake per surface area in $U/cm^2$.

TABLE X

| SAMPLE | THROMBIN UPTAKE $U/cm^2$ |
|---|---|
| PVC Tubing Control (uncoated) | 0.001 |
| PVC Tubing (coated/irradiated/leached in NaCl) | 0.008 |

The results indicated that leaching of the cationic moiety did not remove the heparin and did not destroy the anticoagulant effect of the covalently bound heparin coating.

Having thus described exemplary embodiments of the present invention, it should be noted by those skilled in the art that the disclosures herein are exemplary only and that alternatives, adaptations and modifications may be made within the scope of the present invention.

We claim:

1. A process for reducing the surface thrombogenicity of a medical device having at least one polyvinylchloride surface, said process comprising the steps of:
   providing a solution in an organic solvent of a complex of an anionic heparin moiety and a cationic organic moiety selected from the group consisting of dimethylstearylamine, polyethyleneimine, benzalkonium ion, stearylkonium ion, and tridodecylmethylammonium ion;
   depositing from said solution a uniform and continuous film of said complex upon a polyvinylchloride surface of a medical device; and
   exposing the polyvinylchloride surface having said film deposited thereon to a sufficient dose of ionizing radiation to form covalent bonds between said complex and said polyvinylchloride surface.

2. The process of claim 1 wherein said complex is present in said organic solvent in a concentration of about 0.01 wt % to about 10 wt % of said solution.

3. A process for simultaneously sterilizing a medical device and covalently binding heparin to a blood-contacting polyvinylchloride surface of a medical device, said process comprising the steps of:
   providing a solution in an organic solvent of a complex of an anionic heparin moiety and a cationic organic moiety selected from the group consisting of dimethylstearylamine, polyethyleneimine, benzalkonium ion, stearylkonium ion, and tridodecylmethylammonium ion;
   depositing from said solution a uniform and continuous film of said complex upon a polyvinylchloride surface of a medical device;
   allowing said organic solvent to vaporize; and
   exposing the medical device having said film deposited thereon to a sufficient dose of ionizing radiation to form covalent bonds between said complex and said polyvinylchloride surface and to sterilize said medical device.

4. The process of claim 3 wherein said complex is present in said organic solvent in a concentration of about 0.01 wt % to about 10 wt % of said solution.

5. The process of claim 1 wherein said dose of ionizing radiation is at least 0.1 megarad.

6. The process of claim 1 further including the step, after exposing to ionizing radiation, of contacting said complex covalently bound to said polyvinylchloride surface with an aqueous salt solution having an ionic strength sufficiently high to exchange said cationic organic moiety with a cation of said aqueous salt solution.

7. The process of claim 6 further including the step of sterilizing said medical device.

8. The process of claim 3 wherein said dose of ionizing radiation is at least 1.5 megarad.

9. The process of claim 3 further including the step of packaging said medical device in sterile packaging subsequent to allowing said organic solvent to vaporize.

10. An antithrombogenic medical device prepared according to the process of claim 1.

11. An antithrombogenic medical device prepared according to the process of claim 3.

* * * * *